(12) United States Patent
Weber

(10) Patent No.: US 8,137,373 B2
(45) Date of Patent: Mar. 20, 2012

(54) MEDICAL DEVICES COMPRISING NANOMATERIALS AND THERAPEUTIC METHODS UTILIZING THE SAME

(75) Inventor: Jan Weber, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 122 days.

(21) Appl. No.: 12/418,849

(22) Filed: Apr. 6, 2009

(65) Prior Publication Data

US 2009/0227944 A1    Sep. 10, 2009

Related U.S. Application Data

(63) Continuation of application No. 10/256,388, filed on Sep. 27, 2002, now Pat. No. 7,517,353.

(60) Provisional application No. 60/331,332, filed on Sep. 28, 2001.

(51) Int. Cl.
*A61M 25/00* (2006.01)
*A61M 25/10* (2006.01)

(52) U.S. Cl. ........ 606/194; 606/200; 524/262; 524/267; 524/269; 524/445; 524/496

(58) Field of Classification Search .......... 606/194–200; 604/96.01, 103.09; 623/1.11, 903; 977/905
See application file for complete search history.

(56) References Cited

U.S. PATENT DOCUMENTS

| | | | |
|---|---|---|---|
| 4,762,129 A | 8/1988 | Bonzel | |
| 5,021,515 A | 6/1991 | Cochran et al. | |
| 5,034,252 A | 7/1991 | Nilsson et al. | |
| 5,040,548 A | 8/1991 | Yock | |
| 5,156,594 A | 10/1992 | Keith | |
| 5,195,969 A | 3/1993 | Wang et al. | |
| 5,350,395 A | 9/1994 | Yock | |
| 5,451,233 A | 9/1995 | Yock | |
| 5,534,007 A | 7/1996 | St. Germain et al. | |
| 5,538,510 A | 7/1996 | Fontirroche et al. | |
| 5,554,670 A | 9/1996 | Giannelis et al. | |
| 5,747,560 A | 5/1998 | Christiani et al. | |
| 5,749,888 A | 5/1998 | Yock | |
| 5,797,877 A | 8/1998 | Hamilton et al. | |

(Continued)

FOREIGN PATENT DOCUMENTS

EP    1 388 346 A1    2/2004

(Continued)

OTHER PUBLICATIONS

Bandyopadhyaya, Rajdip et al., "Stabilization of Individual Carbon Nanotubes in Aqueous Solutions," Nano Letters, vol. 2, No. 1 (2002) pp. 25-28.

(Continued)

*Primary Examiner* — Elizabeth Houston
(74) *Attorney, Agent, or Firm* — Seager, Tufte & Wickhem, LLC

(57) ABSTRACT

The present invention provides medical devices comprising nanomaterials. By utilizing nanomaterials in the production thereof, the inventive medical devices can be provided with various advantageous properties and/or capabilities. Methods of producing the inventive medical devices are also provided. Inasmuch as the inventive devices are expected to provide certain advantages in their use, there is also provided a method of medical care, including methods of treatment or diagnosis, wherein the inventive devices are brought into therapeutic contact with a body to be treated or diagnosed thereby.

14 Claims, 2 Drawing Sheets

U.S. PATENT DOCUMENTS

| | | | |
|---|---|---|---|
| 5,811,447 A | | 9/1998 | Kunz et al. |
| 5,836,926 A | | 11/1998 | Peterson et al. |
| 5,843,032 A | | 12/1998 | Kastenhofer |
| 5,853,886 A | | 12/1998 | Pinnavaia et al. |
| 5,942,638 A | | 8/1999 | Lichtenhan et al. |
| 5,948,843 A | | 9/1999 | Boutier et al. |
| 5,980,486 A | | 11/1999 | Enger |
| 5,980,533 A | * | 11/1999 | Holman ............ 623/1.11 |
| 6,001,118 A | | 12/1999 | Daniel et al. |
| 6,010,521 A | | 1/2000 | Lee et al. |
| 6,016,848 A | | 1/2000 | Egres, Jr. |
| 6,124,273 A | | 9/2000 | Drohan et al. |
| 6,126,740 A | | 10/2000 | Schulz et al. |
| 6,129,708 A | | 10/2000 | Enger |
| 6,129,739 A | | 10/2000 | Khosravi |
| 6,132,824 A | * | 10/2000 | Hamlin ............ 428/35.2 |
| 6,156,350 A | | 12/2000 | Constantz |
| 6,245,849 B1 | | 6/2001 | Morales et al. |
| 6,252,020 B1 | | 6/2001 | Kuo et al. |
| 6,331,262 B1 | | 12/2001 | Haddon et al. |
| 6,331,265 B1 | | 12/2001 | Dupire et al. |
| 6,336,934 B1 | | 1/2002 | Gilson et al. |
| 6,350,805 B1 | | 2/2002 | Korbee et al. |
| 6,368,569 B1 | | 4/2002 | Haddon et al. |
| 6,414,086 B1 | | 7/2002 | Wang et al. |
| 6,417,262 B1 | | 7/2002 | Turner et al. |
| 6,447,439 B1 | | 9/2002 | Vallana et al. |
| 6,503,958 B2 | | 1/2003 | Hughes et al. |
| 6,520,952 B1 | | 2/2003 | Jimenez |
| 6,569,932 B2 | | 5/2003 | Hsiao et al. |
| 6,586,548 B2 | | 7/2003 | Bonafini, Jr. et al. |
| 6,653,365 B2 | | 11/2003 | Jia |
| 6,737,447 B1 | | 5/2004 | Smith et al. |
| 6,740,191 B2 | | 5/2004 | Clarke et al. |
| 6,793,994 B2 | | 9/2004 | Tsai et al. |
| 6,833,392 B1 | | 12/2004 | Acquarulo, Jr. et al. |
| 6,905,511 B2 | | 6/2005 | Wang et al. |
| 7,091,297 B2 | | 8/2006 | Mather et al. |
| 2001/0009769 A1 | | 7/2001 | Williams et al. |
| 2002/0011030 A1 | | 1/2002 | Williams et al. |
| 2002/0014182 A1 | | 2/2002 | Yadav et al. |
| 2002/0022678 A1 | | 2/2002 | Lan et al. |
| 2002/0049495 A1 | | 4/2002 | Kutryk et al. |
| 2002/0086896 A1 | | 7/2002 | Kunz et al. |
| 2002/0137834 A1 | | 9/2002 | Barbee et al. |

FOREIGN PATENT DOCUMENTS

| | | |
|---|---|---|
| GB | 2 285 401 A | 7/1995 |
| WO | 93/11190 A1 | 6/1993 |
| WO | 96/18686 A1 | 6/1996 |
| WO | 98/30604 A1 | 7/1998 |
| WO | 99/38914 A3 | 8/1999 |
| WO | 99/41299 A1 | 8/1999 |
| WO | 00/57932 A2 | 10/2000 |
| WO | 01/30864 A2 | 5/2001 |
| WO | 01/34685 A1 | 5/2001 |
| WO | 01/48080 A1 | 7/2001 |
| WO | 01/87193 A1 | 11/2001 |

OTHER PUBLICATIONS

Dagani, Ron et al., "Sugary Ways to Make Nanotubes Dissolve," Science & Technology, vol. 80, No. 28, Jul. 15, 2002, 5 sheets.

Dzenis, Yuris et al., "Continuous Carbon Nanofibers for Nanofiber Composites," Mat. Res. Soc. Symp. Proc., vol. 702 (2002) pp. U5.4.1-U5.4.6.

Fu, Bruce X. et al., "Nanoscale Reinforcement of Polyhedral Oligomeric Silsesquioxane (POSS) in Polyurethane Elastomer," Polym Int, vol. 49 (2000) pp. 437-440.

Fu, Bruce X. et al., "Structural Development During Deformation of Polyurethane Containing Polyhedral Oligomeric Silsesquioxanes (POSS) Molecules," Polymer, vol. 42 (2001) pp. 599-611.

O'Connell, Michael J. et al., "Reversible Water-Solubilization of Single-Walled Carbon Nanotubes by polymer Wrapping," Chemical Physics Letters, vol. 342 (2001) pp. 265-271.

Pompeo, Francisco et al., "Water Solubilization of Single-Walled Carbon Nanotubes by Functionalization with Glucosamine," Nano Letters, vol. 2, No. 4 (2002) pp. 369-373.

Star, Alexander et al., "Starched Carbon Nanotubes," Angew. Chem. Int. Ed., vol. 41, No. 14 (2002) pp. 2508-2512.

Wilson, Dr. Phillip S., "Nano-Composite Market Opportunities," Inspired Innovations, L.L.C., dated before Sep. 27, 2002, 9 sheets.

Bins, Peter et al., "Nanocomposite Market Opportunities," Bins & Associates (2001) 8 sheets.

Product Information Pamphlet, "Carbon Nanotube Technology," CSIRO, Division of Molecular Science, Victoria, AU, dated before Sep. 27, 2002, 2 sheets.

\* cited by examiner

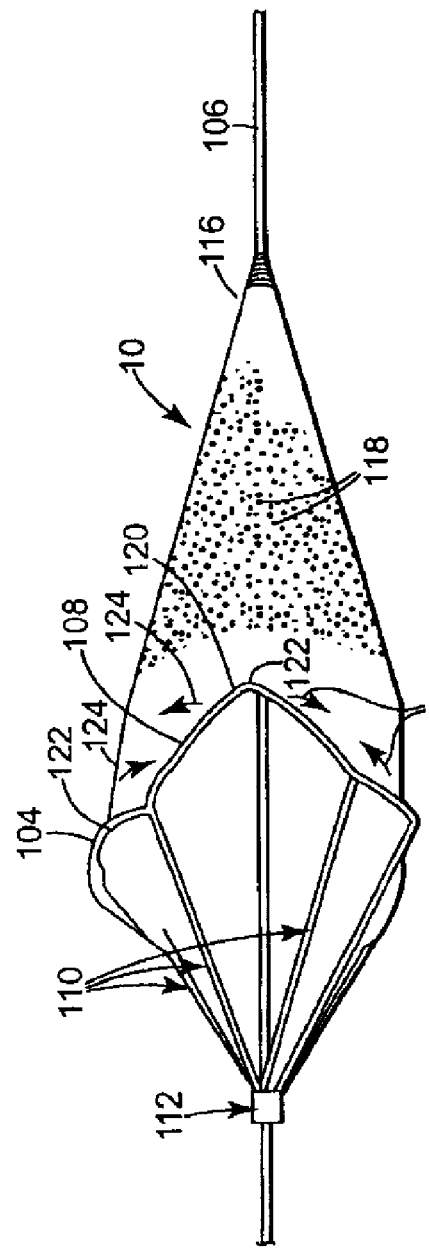
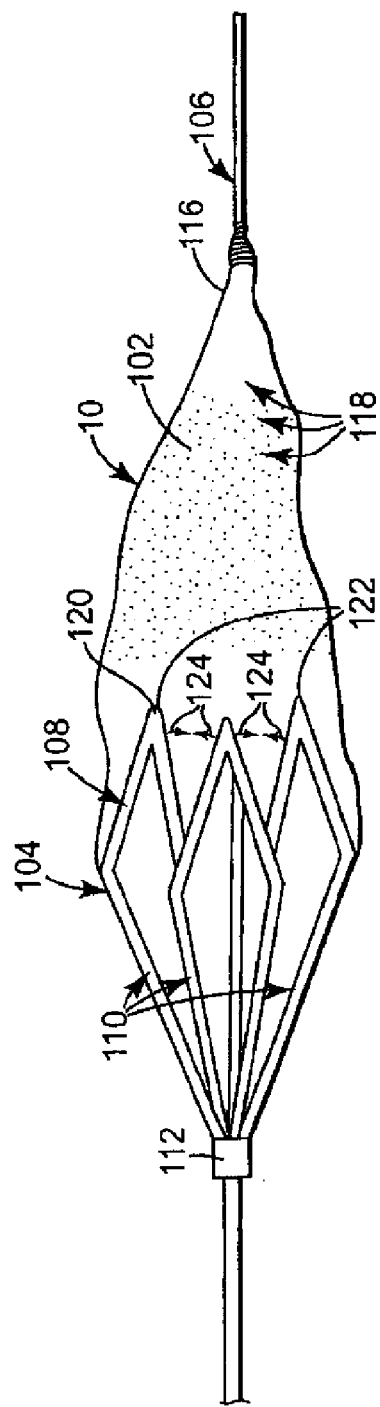

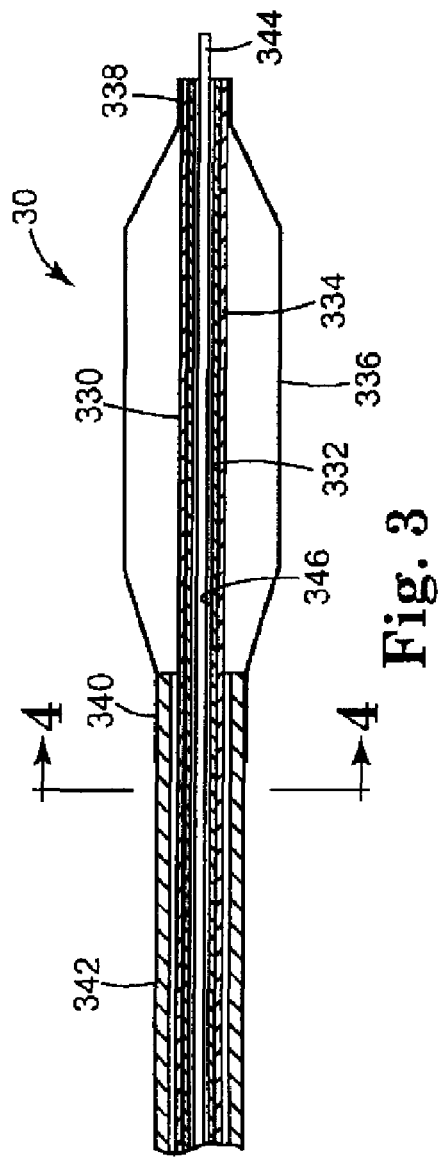
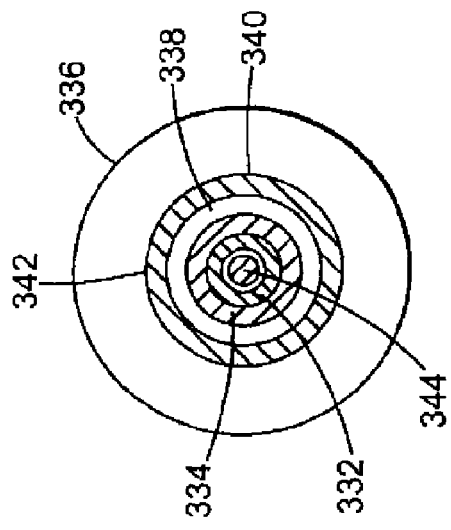

MEDICAL DEVICES COMPRISING NANOMATERIALS AND THERAPEUTIC METHODS UTILIZING THE SAME

CROSS REFERENCE TO RELATED APPLICATIONS

This application is a continuation of U.S. application Ser. No. 10/256,388, filed Sep. 27, 2002; which claims the benefit of U.S. Provisional Application Ser. No. 60/331,332, filed Sep. 28, 2001; and also claims the benefit of U.S. Provisional Application Ser. No. 60/327,629, filed Oct. 5, 2001; the entire disclosures of which are all incorporated herein by reference.

FIELD OF THE INVENTION

The present invention relates to medical devices including one or more components comprising one or more nanoparticles and/or nanocomposite materials. By utilizing these nanomaterials in the manufacture of the inventive medical devices, certain properties of the nanoparticles and/or nanocomposites may be exploited in ways particularly advantageous in the medical device industry.

BACKGROUND OF THE INVENTION

The medical device industry is but one example of an industry where the products or devices produced and used therein requires the products to exhibit a diverse array of properties and/or capabilities. Transluminal medical devices are one example. Such devices are typically introduced into the vasculature of a patient at a point remote from the treatment site, a procedure that can be uncomfortable for the patient. In order to perform acceptably, and to minimize the trauma to the patient, transluminal devices typically exhibit diverse, and at times divergent, performance characteristics and perform a wide range of functions.

For example, many such devices desirably exhibit good maneuverability so as to be manipulated to and/or inserted at a location requiring treatment, but yet sufficiently strong in the longitudinal direction so as not to buckle or kink when being so manipulated. In fact, many medical devices require a combination of these, and other, properties such as strength, thermal stability, structural stability, flexibility, opacity, radio-opacity, storage stability, lubricity, stability to sterilization treatment, etc., in order to be effective for their intended purpose. Often medical devices are further desirably biodegradable, capable of delivering therapeutic agents, etc.

Material selection is thus very important to the therapeutic efficacy of many medical devices since the properties of the materials used often dictates the properties and/or capabilities of the overall device. However, the range of properties available from one, or even a combination of, material(s) is often not as broad as would be desired to provide a corresponding breadth of properties or capabilities in medical device applications. As a result, many medical devices need to be manufactured from a combination of materials, processed in a specific manner, or subjected to other treatments, in order to exhibit the desired and/or required characteristics.

Thus, there is a continuing need in the medical device industry to develop or discover additional materials that exhibit the range of properties or capabilities required or desired for a medical device.

SUMMARY OF THE INVENTION

The present invention provides medical devices comprising nanoparticles and/or nanocomposite materials. According to the invention, the utilization of such nanomaterials in the manufacture of medical devices can provide the inventive devices with many, or all, of the diverse properties and/or capabilities often desirable in the same. That is, inasmuch as such devices often desirably exhibit a vast number of often times divergent properties, and/or desirably perform a variety of functions, it can be difficult to manufacture such devices without utilizing an extensive number of materials and processing techniques. By employing the present invention, however, medical devices can be produced with a desired array of properties and/or capabilities using a lesser amount of materials and/or processing techniques, or medical devices can be produced wherein one or more of the properties and/or capabilities are enhanced.

As a result, the present invention provides a medical device comprising at least one nanomaterial. The nanomaterial, in turn, may comprise at least one plurality of nanoparticles and/or at least one nanocomposite. The nanomaterial(s) may be present in one or more components of the device, or may be utilized to produce the device in total. Further, the nanomaterial(s) may be present as a tie layer, a coating or any other layer of the component or overall device. In certain advantageous embodiments, the nanoparticles may comprise a therapeutic agent.

Exemplary medical devices to which the invention is particularly directed include balloons, catheters, shafting, filters and stent delivery systems such as disclosed in U.S. Pat. Nos. 5,843,032; 5,156,594; 5,538,510; 4,762,129; 5,195,969; 5,797,877; 5,836,926; 5,534,007; 5,040,548; 5,350,395; 5,451,233; 5,749,888; 5,980,486; and 6,129,708, the full disclosures of each which are hereby incorporated by reference herein for all purposes.

Also provided is a method of making the inventive medical devices wherein the method comprises selecting a nanoparticle and/or nanocomposite material and preparing at least a component of the medical device from the nanomaterial. The method may optionally include the steps of identifying the desired components of the nanoparticle and/or nanocomposite and preparing the nanomaterial according to any known technique.

In one aspect, the disclosure features medical care kits that include at least one medical device and at least one nanomaterial provided in packaging. For example, the at least one nanomaterial can be included in at least a component of the at least one medical device. The nanomaterial can include, e.g., a first plurality of nanoparticles, such as at least one biodegradable, biocompatible material, and at least one therapeutic agent. The first plurality of nanoparticles can, e.g., further include a magnetic material. The first plurality of nanoparticles can, e.g., further include a heat sensitive material. For example, the medical device can be a stent, the at least one nanomaterial including a coating applied to the at least a portion of the stent and the nanomaterial coating including a thermoplastic matrix material and magnetic nanoparticles.

The inventive medical devices can have enhanced properties and/or capabilities relative to or properties and/or capabilities absent from a corresponding medical device not comprising a nanomaterial. As a result, the inventive medical devices can provide certain advantages in their use. In this regard, the present invention also provides a method of treatment or diagnosis comprising bringing a medical device into therapeutic contact with a body to be treated or diagnosed, wherein the medical device comprises at least one nanomaterial.

BRIEF DESCRIPTION OF THE DRAWINGS

The accompanying drawings, which are incorporated in and constitute a part of this application, illustrate several aspects of the invention and together with description of the embodiment reserve to explain the principles of the invention. A brief description of the drawings is as follows:

FIG. 1 is a longitudinal view, taken partially in cross-section, of a medical device in accordance with the present invention wherein the medical device is shown in a closed profile for insertion into a bodily lumen;

FIG. 2 is a longitudinal view, taken partially in cross-section, of a medical device in accordance with the present invention wherein the medical device is shown in an open, radially expanded profile;

FIG. 3 is a longitudinal cross-sectional view of the distal end of a medical device in accordance with the present invention;

FIG. 4 is a transverse cross-sectional view of the device shown in FIG. 3, taken at line 4-4.

DETAILED DESCRIPTION OF EMBODIMENTS OF THE INVENTION

The embodiments of the present invention described below are not intended to be exhaustive or to limit the invention to the particular embodiments disclosed in the following detailed description. Rather, the embodiments are described so that others skilled in the art understand the principles and practices of the present invention.

The nature of the production and therapeutic use of many medical devices can require that the devices exhibit a broad and diverse array of properties and/or be capable of performing many functions. In order to achieve such a combination of desired properties and/or capabilities, more than one type of material is often employed in the construction of medical devices. For example, reinforcing particles can be applied or added to a substrate or matrix material to form a composite material having a desired property, such as strength or an adhesion quality, otherwise lacking at the surface, or within the body of a matrix material. Conventionally, the particles used in such composites are comprised of glass fibers, aggregates of amorphous or graphitic carbon, metal flakes, etc., and are at least about 1 micrometer in diameter in their largest dimension, or larger. While such composite materials are useful in many medical device applications, the allowed tolerances in the manufacture of many other medical devices may not accommodate conventional, large size, filler particles.

Recently, a new class of particles has been described having at least one dimension less than about 1 micrometer. It has now been discovered that these much smaller particles are particularly advantageously employed in medical device applications. The present invention thus provides medical devices comprising one or more of these nanomaterials.

As used herein, the term 'nanoparticle' is meant to indicate a particle having a greatest dimension of less than 1 micrometer. The nanoparticles may be comprised of one or more materials, may be formed by using any processing technique, and may have any geometry, i.e., the nanoparticles can be generally spherical, octagonal or hexagonal, or they may be in the form of nanotubes, nanobelts, nanofibers, or nanowires, and may be solid, hollow or porous, depending upon the desired application. Typically, the nanoparticles suitable for use in the inventive medical devices, either alone or as a component of a nanocomposite material, have at least one dimension less than about 1000 nm in size. In some embodiments, the nanoparticles can advantageously have one dimension of less than about 750 nm, typically less than about 500 nm, for example, from about 1 nm to about 100 nm.

The term 'nanocomposite' generally refers to a composite material comprising at least one plurality of nanoparticles operatively disposed relative to a matrix material. The plurality of nanoparticles may be dispersed throughout the matrix material, either uniformly or otherwise, or may be substantially aggregated relative to a surface of the matrix material. Advantageously, the load or density of nanoparticles so disposed relative to the matrix material may be caused to vary across one or more dimensions of the matrix material as incorporated within the inventive medical devices, so that the property or capability enhanced or imparted by virtue of the use of the nanocomposite material within the inventive device can correspondingly vary. Finally, the term 'nanomaterial' is intended to indicate either or both nanoparticles and nanocomposites. That is, a medical device in accordance with the present invention comprising at least one nanomaterial may comprise only a plurality of nanoparticles, only a nanocomposite, or both.

For example, a medical device in accordance with the present invention wherein the nanomaterial comprises at least one plurality of nanoparticles would include a plurality of nanoparticles further comprising a therapeutic agent and a magnetic material and/or a heat sensitive thermoplastic material provided in combination with a device capable of attracting and/or adhering the nanoparticles thereto. Advantageously, this embodiment of the inventive medical device allows for the delivery of a therapeutic agent systemically, that can yet be delivered to, and substantially remain at, a desired treatment site at any desired time.

For example, such a plurality of magnetized nanoparticles could be provided with a magnetized device, such as a stent or graft, that is itself magnetized, coated or wrapped with a magnetic material, such as a magnetized wire, or operably disposed relative to one or more magnets or other magnetized materials. Such a magnetized stent or graft could be delivered and or inserted at a desired treatment site, and prior to, during, or at any time after delivery of the stent or insertion of the graft, the magnetized nanoparticles could be caused to bind to the stent or graft via magnetic forces. For example, the magnetized nanoparticles could be injected as a solution local to the stent or graft, could be injected systemically, or could be delivered via a perfusion balloon catheter.

Advantageously, such a delivery of magnetized nanoparticles could be caused to occur at any time during the resident life of the stent or graft. Further advantages of this embodiment of the invention include the ability to systemically and yet directedly deliver any amount or number of therapeutic agents, as well as the ability to deliver such agents to a treatment site comprising a device that may not otherwise be incorporated into the device, e.g., therapeutic agents that are sterilization sensitive, such as DNA, proteins, viruses, and the like. Finally, just as this embodiment of the invention allows for the systemic delivery of therapeutic agents at any time, it similarly is envisaged that this embodiment of the invention could allow for the removal of therapeutic agent from the treatment site. That is, a collection device capable of generating a stronger magnetic field than that of the device could be removably delivered to the treatment site to attract and adhere the magnetized nanoparticles, and thus, any remaining therapeutic agent.

Further, in this embodiment of the invention, the nanoparticles may further comprise a heat sensitive thermoplastic material, either in place of or in combination with the magnetic material. The desired device could then be operatively disposed relative to an energy source, so that the nanoparticles may be systemically delivered, and once carried to the desired treatment site the energy source may be activated, thereby heating the device and/or the nanoparticles. As a result, the heat sensitive material included in the nanoparticles can be caused to soften and adhere to at least a portion of a surface of the device.

Yet another example wherein an inventive medical device may comprise a plurality of nanoparticles, not necessarily incorporated within or disposed relative to a matrix material, would include those embodiments of the invention wherein the nanoparticles are provided as a 'tie-layer' between two layers of the inventive device. One particular example of such an embodiment would include the utilization of carbon or ceramic nanotubes or fibers as a tie layer between two layers that are desirably heat welded, coextruded, spun, sprayed or otherwise caused to be bonded together. In particular, a layer of such nanoparticles may be deposited on a first layer, either randomly as may occur by dipping a first layer into a solution of such nanoparticles, or in a relatively patterned or uniform fashion, such as a braid, as may be formed by spinning or spraying the nanoparticles on the first layer or surface. The second layer would then be deposited as desired, and via the method of application of the second layer or the subsequent application of heat, as by e.g., heat welding, portions of the nanoparticles would become at least partially intertwined in either or both of the first and second layers of material, the resulting bond between the first and second layers being strengthened thereby. Clearly, this embodiment may also be encompassed within that embodiment of the invention wherein the medical devices comprise at least one nanocomposite material, inasmuch as the uniform dispersion, or in fact any dispersion, of nanoparticles throughout a matrix material is not required to fall within the definition of the term 'nanocomposite' as that term is used herein.

The nanomaterial to be used in the present medical devices is not particularly restricted. Rather, any nanomaterial that can be prepared or engineered to provide or enhance at least one property desired in the desired medical device, or to provide a medical device with a desired capability, can be used. The selection of the particular nanoparticles, or the nanoparticles and matrix material(s), for use in the nanomaterial(s) will depend on the intended use of the medical device into which the nanomaterial will be incorporated and the desired properties of a device to be used in that manner.

Additionally, the manner in which the nanocomposite is incorporated into the overall device can further be engineered and optimized in order to achieve or enhance desired properties and/or capabilities in the inventive medical device. For example, in a multilayered device, one layer of the device could be a nanomaterial, with the remaining layers being comprised of traditionally filled materials, non-composite materials, or a combination of these. Further, the number and organization of the layers can be chosen to optimize and/or to provide properties desired in the device.

Generally speaking then, a matrix material according to the invention may be any material suitable, or later determined to be suitable, for use in such a medical device. The matrix material may be any material that is historically or currently utilized, or contemplated for future use, in a corresponding medical device not comprising a nanocomposite component. The matrix material may be comprised of organic, inorganic or hybrid organic/inorganic materials.

Additionally, the matrix material may be a single material or a combination of materials, e.g., the matrix material may be a metal alloy, copolymer or polymer blend.

Exemplary matrix materials include, for example, polymers, such as thermoplastics and thermosets. Example thermoplastics suitable for use as a matrix material include, for example, polyolefins, polyamides, polyesters, polyethers, polyurethanes, polyureas, polyvinyls, polyacrylics, fluoropolymers, copolymers and block copolymers thereof, and mixtures thereof. Representative examples of thermosets that may be utilized as a matrix material include elastomers such as EPDM, epichlorohydrin, nitrile butadiene elastomers, silicones, etc. Conventional thermosets such as epoxies, isocyanates, etc., can also be used. Biocompatible thermosets may also be used, and these include, for example, biodegradable polycaprolactone, poly (dimethylsiloxane) containing polyurethanes and ureas, and polysiloxanes.

Analogously, nanoparticles according to the invention may be comprised of any material, or combination of materials, suitable, or later determined to be suitable, for use in a medical device, so long as the greatest dimension of the nanoparticles measures 1000 mm or less, typically 750 mm or less, more typically 500 nm or less, for example, from about 1 mm to about 100 mm. The nanoparticles may comprise any material that has been, is, or is contemplated for use as a conventionally sized filler material in a medical device. Desirably, the nanoparticles comprise a material capable of at least minimally altering the physical, mechanical, chemical, or other properties of a matrix material when incorporated therein, or of enhancing or providing the inventive medical device with a desired capability.

As such, the nanoparticles may be comprised of any one or combination of organic, inorganic, or hybrid organic/inorganic materials. Additionally, the nanoparticles may be a single material or a combination of materials. For example, the nanoparticles may comprise a metal alloy, copolymer or polymer blend, or may comprise at least a biocompatible and biodegradable material and a therapeutic agent. This latter embodiment may be advantageously employed in those applications where the systemic delivery of therapeutic agents to a treatment site is deserved.

Examples of materials suitable for use in the nanoparticles include, among others, synthetic or natural smectic phyllosilicates including clays and micas (that may optionally be intercalated, exfoliated and/or otherwise chemically modified) such as montmorillonite (mmt), hectorites, hydrotalcites, vermiculite, and laponite; monomeric silicates such as polyhedral oligomeric silsesquioxanes (POSS) including various functionalized POSS and polymerized POSS; carbon and ceramic nano-tubes, nano-wires and nano-fibers, including carbon nanofibers and nanotubes of any geometry prepared by electrospinning a carbonizable material, such as polyacrylonitrile; single and multi-walled fullerene nanotubes, silica nanogels, and alumina nano-fibers, as well as metal and metal oxide powders including aluminum oxide ($AlO_3$), titanium oxide ($TiO_2$), tungsten oxide, zirconium oxide, gold (Au), silver (Ag), platinum (Pt) and magnetic or paramagnetic materials such as neodinium iron boron or super paramagnetic ferrite oxide ($Fe_3O_4$) or super paramagnetic maghemite ($Fe_2O_3$); organic materials including temperature sensitive polymers, such as polyvinylpyrrolidone and n-isopropylacrylamide copolymers or blends, and poloxamer, biodegradable polymers such as poly(lactic) acid, polysaccharide, polyalkylcyanoacrylate, which biodegradable polymers may also be magnetized; and further including polytetrafluoroethylene, and dendrimers or dendrimer metal complexes.

The amount of the nanoparticles, or combinations of nanoparticles comprised of different materials, to be incorporated into the matrix or inventive medical device can vary depending on the desired properties exhibited by a particular medical device or medical device component. Generally speaking, enough of the nanoparticles should be included so that desired property(ies) and/or capability(ies) are at least minimally exhibited by the nanocomposite and/or the medical device. On the other hand, not so much of the nanoparticles should be included so as to have a detrimental effect on the properties of the nanocomposite and/or medical device.

With this in mind, and while the particular range may vary depending on the nanoparticles and matrix material being utilized, or further on the desired properties or capabilities of the inventive medical device, it is believed that a useful range of nanoparticles for inclusion in the inventive medical devices is from about 0.005% weight to about 99% weight of the total weight of the nanocomposite or overall medical device, as the case may be. In many embodiments, nanoparticles may be incorporated in an amount of from about 0.01% up to about 40% or 50% by weight and as a percentage of the total weight of the nanocomposite and/or medical device, as the case may be. In a typical embodiment, the nanoparticles can be incorporated in an amount of from about 0.1% to about 20% by weight of the nanocomposite or medical device, for example, from about 1% to about 10% by weight of the nanocomposite or medical device.

The present invention further contemplates that there may be applications in which it will be desirable to have a combination of more than one plurality of nanoparticles, so that each different plurality may be comprised of a different material or combination of materials. In this manner, a further enhancement of a single desired property or an addition of a new property or capability may be seen in the inventive medical device.

For example, it may be advantageous to prepare a nanocomposite comprising a polymeric matrix material and a first plurality of nanoparticles that exhibits radio-opacity. The nanocomposite, or inventive device itself, may desirably further comprise a second plurality of nanoparticles that comprises a strength enhancing material. A device according to this embodiment of the invention would not only be visible via conventional imaging techniques, but further, could exhibit enhanced strength relative to a corresponding device not comprising the strength enhancing nanoparticles.

As but one particular example of this embodiment of the invention, a stent could be provided that is coated with a nanocomposite prepared with an appropriate matrix material and a first plurality of magnetic nanoparticles. A second plurality of nanoparticles comprising a magnetized biodegradable, biocompatible material, such as magnetized polylactic acid, and a therapeutic agent could also be provided. As described above, the stent could then be implanted at the desired treatment site, and the second plurality of particles could be delivered systemically either concurrent with, or subsequent to, the delivery of the stent. The magnetic materials of the stent and the second plurality of nanoparticles could attract each other and adhere at least a portion of the second plurality of nanoparticles to the stent. As also described above, it is not necessary that the stent comprise magnetic nanoparticles, or any nanomaterial at all, rather small magnets could be operatively provided in connection with the stent.

This embodiment thus not only provides for the targeted and perhaps even controlled delivery of therapeutic agents to a desired treatment site, but further, provides the opportunity to systemically deliver the therapeutic agent at any desired time. That is, whereas prior art medical devices achieve drug delivery by incorporating the drug in a timed release coating on the device, thereby limiting the time within which the drug is delivered to the time that the device is utilized or implanted and for a short time period thereafter, this embodiment of the present invention would allow for the delivery of therapeutic agents to a desired treatment site long after the implantation of the inventive medical device.

In those embodiments of the present invention wherein the nanoparticles desirably comprise a therapeutic agent, any therapeutic agent may be incorporated relative thereto. The therapeutic agent can be genetic or non-genetic or may comprise cells or cellular matter. Examples of non-genetic therapeutic agents include, but are not limited to, antithrombogenic agents such as heparin and its derivatives, urokinase, and dextrophenylalanine proline arginine chloromethylketone (Ppack); anti-proliferative agents such as enoxaprin, andiopeptin, or monoclonal antibodies capable of blocking smooth muscle cell proliferation, hirudin, and acetylsalicylic acid; anti-inflammatory agents such as desamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatine and thymidine kinase inhibitors; anesthetic agents such as lidocaine, bupivacaine, and ropivacaine; anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms. Examples of genetic materials that can be used as therapeutic agents include, but are not limited to, anti-sense DNA or RNA; and DNA coding for anti-sense RNA, tRNA or rRNA, e.g., to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet derived growth factor, tumor necrosis factor α, hepatocyte growth factor and insulin like growth factor, cell cycle inhibitors including CD inhibitors, agents useful for interfering with cell proliferation such as thymidine kinase, and the family of bone morphogenic proteins (BMP), or any other molecule capable of inducing an upstream or downstream effect of a BMP, including BMP-2, BMP-3, BMP-4, BMP-5, BMP-6 (Vrg-1), BMP-7 (OP-1), BMP-8, BMP-9, BMP-10, BMP-11, BMP-12, BMP-13, BMP-14, BMP-15 and BMP-16.

The properties and/or capabilities of the nanocomposites and/or inventive medical devices may be affected by compatibility of, and/or the level and/or kind of interaction that occurs between, the nanoparticles and the matrix material of the nanocomposite, or of the nanoparticles and the inventive medical device. For example, the nanoparticles and matrix material and/or the device may also interact chemically, such as by the establishment of Van Der Waal's forces, covalent bonds or ionic bonds between the filler particles and the matrix material.

Or, the compatibility may be such that the nanoparticles and the matrix and/or medical device interact physically, such as by chain entanglement of the nanoparticles with the matrix material and/or the surface of the medical device via the physical interaction of the device and the heat sensitive polymer. For example, in that embodiment of the invention wherein the nanoparticles comprise a heat sensitive polymer and a therapeutic agent, a source of heat external to a medical device implanted within a host could be used to cause the heat sensitive polymer of the nanoparticle to soften and adhere to the medical device via the physical interaction of the device and the heat sensitive polymer. Said softening could also assist in the release of the therapeutic agent, and thus such an inventive medical device could be utilized to provide for targeted drug delivery. As another example, in that embodiment of the invention where the nanoparticles comprise a magnetic material, physical interaction could be caused to occur with the surface of a medical device via the provision of magnets operatively disposed relative to a surface of the medical device. If the magnetic material were further a biodegradable magnetic material, and the nanoparticle further included a therapeutic agent, targeted, timed, and controlled drug delivery could be provided by the device.

Generally speaking, any such compatibility, and the resulting interaction, can act to enhance the dispersion of the nanoparticles within the matrix material of a nanocomposite and/or to enhance the disposition of the nanoparticles relative to the medical device. If this is the case, and very generally speaking, the greater the compatibility, the greater the increased dispersion and/or enhanced disposition. Therefore, in applications where such greater dispersion or enhanced disposition would be desirable, the compatibility of, and resulting interaction between, the nanoparticles with the matrix material and/or the medical device can be encouraged or facilitated.

The compatibility of the nanoparticles and the matrix material can be enhanced, for example, simply by selection of the materials for use as the matrix or in the nanoparticles. That is, interaction between the nanoparticles and the matrix may be facilitated or caused simply by selecting nanoparticles and matrix materials, and/or other medical device material(s), with compatible functional groups. If such compatible functional groups are not present, they can be provided by 'functionalizing' the nanoparticles matrix material or desired surface of the medical device to provide compatible functional groups that can then interact with each other.

Smectic phyllosilicates, monomeric silicates, and ceramics are just a few representative examples of materials suitable for use in the nanoparticles that may be advantageously functionalized to provide increased interaction between the nanoparticles and the matrix material and/or medical device. For example, POSS monomers can be functionalized with, e.g., organic side chains (e.g., methyl groups, aminopropyl groups or polymeric side chains, see, e.g., Examples 1 and 2, below) to enhance compatibility with, e.g., polystyrene. Furthermore, clays, such as montmorillonite may be functionalized with alkylammonium so that the montmorillonite is capable of interacting with a polyurethane, for example. Clays may further be functionalized with block or graft copolymers wherein one component of the copolymer is compatible with the clay and another component of the copolymer is compatible with the polymer matrix.

In addition to functionalizing any or all of the nanoparticles, the matrix material, or the surface of the inventive device itself, the compatibility of, and interaction between, the nanoparticles, matrix material and/or medical device can be enhanced by incorporating one or more coupling or compatibilizing agents into the nanocomposite, or onto the surface of the inventive device itself. As used herein, the term(s) coupling/compatibilizing agents include any agent capable of enhancing compatibility and/or promoting interaction between the nanoparticles and the matrix material, or between the nanoparticles and the inventive device.

Such agents can be organic or inorganic. The selection of these optional agents will, of course, depend on the nanoparticles, matrix material, and/or the nature of the portion of the inventive device with which the nanoparticles desirably interact. Bearing this in mind, suitable organic coupling agents can be both low molecular weight molecules and polymers. Examples of low molecular weight organic coupling/compatibilizing agents include, but are not limited to, amino acids and thiols. Examples of polymeric compatibilizers would include functionalized polymers, such as maleic anhydride containing polyolefins or maleimide-functionalized polyamides. Inorganic coupling agents would include, for example, alkoxides of silicon, aluminum, titanium, and zirconium, or magnetic powders such as ferrite oxide, to name a few.

Generally speaking, the amount of a coupling/compatibilizing agent used, if used at all, will desirably be that amount which will at least marginally improve the compatibility of the nanoparticles and the matrix material, or the nanoparticles and the inventive medical device itself, so that at least a minimal enhancement of the dispersion of the nanoparticles within the matrix and/or the properties of the nanocomposite, or an enhanced interaction between the nanoparticles and the inventive device, can be observed. Useful amounts of such agents are contemplated to be within the ranges of from about 0.1% to about 10% by weight of the nanocomposite; typically from about 0.5% to about 7.5%, more typically from about 1% to about 5% by weight of the nanocomposite.

In addition to material selection, functionalizing and compatabilizing as a means to promote interaction of the nanoparticles and the matrix material, said interaction may be enhanced, if desired, by utilizing compatibility enhancing methods of processing such as ultrasonic assisted extrusion and/or compounding. By applying an ultrasonic vibration to the extruder die, for example, the friction shear forces can be reduced, and a melt comprising the matrix material and nanoparticles rendered more homogeneous. Additionally, the nanoparticles and/or matrix material can be dispersed in a solvent, e.g., dimethylformamide, dichloroethylene, N-methyl-2-pyrrolidone and the like. Once so dispersed, the nanoparticle solution and the matrix material solution could be mixed and applied onto a mandrel via electro, or electrohydrodynamic spraying or spinning, or any other suitable method to produce a nanocomposite material or inventive medical device exhibiting enhanced dispersion of the nanoparticles. Any other techniques of enhancing the dispersion of nanoparticles within a matrix can also be utilized, if such an enhanced dispersion is desirable in the chosen application.

While it may be desirable in certain applications to increase the interaction between the nanoparticles and the matrix material or between the nanoparticles and the device itself, extensive interaction between the nanoparticles themselves can be undesirable in certain applications. In particular, in applications where the nanoparticles desirably form a layer with a substantially uniform thickness, or where an otherwise substantially uniform dispersion throughout a matrix material or relative to a medical device is desired, any substantial agglomeration of the nanoparticles can be suboptimal. In such applications then, it may be advantageous or desirable to include a dispersant in the solution with the nanoparticles prior to their dispersion within or application to, the matrix material and/or the inventive device.

In addition to the nanoparticles, the matrix material, and optionally, coupling/compatibilizing agents or dispersants, the nanocomposites and/or medical devices according to the invention can comprise any other materials utilized in a corresponding medical device not comprising a nanomaterial. For example, pigments and/or whiteners can be provided. Also, processing aids, such as plasticizers, surfactants and stabilizers, can be included in the nanocomposites. Also, conductive, magnetic and/or radiopaque agents could be included. Such agents, the amounts in which they are useful, as well as the benefits that they provide, are well known to those of ordinary skill in the art.

One example of a class of stabilizers that may find use in the inventive medical devices and methods is that commonly referred to as radiation oxidative degradations, or "ROD" stabilizers. As the name suggests, these agents may assist a polymer within which they are incorporated to resist any degradation that may otherwise occur upon exposure of the polymer to sterilizing radiation. Additionally, however, such stabilizers may also be useful in assisting a polymer to resist any degradation that may otherwise occur during processing, such as during mixing and/or heating that may be required in order to adequately disperse nanoparticles throughout a matrix material.

Such ROD stabilizers may be antioxidants, particularly radical or oxygen scavengers. Mercapto compounds, hindered phenols, phosphites, phosphonites and hindered amine antioxidants are among the most effective such stabilizers. Specific examples of stabilizers are 2-mercaptobenzimidazole, trilauryl phosphite, IONOX 330, 2-mercaptobenzothiazole, N,N-di(β-napthyl-p-phenylenediamine) (DPPD), SANTONOX R, SANTOWHITE powder, phenothiazine, IONOL, 2,6-di-t-butylcresol, N-cyclohexyl-N'-phenyl-p-phenylenediamine, nickel dibutyldithiocarbamate, IRGANOX 1010, P-(3,5-di-t-butyl-6-hydroxyphenyl) propionate, 1,2,2,6,6-pentamethyl-4-stearoyl piperidine, and 2,2,6,6, tetramethyl-4-nitropiperidine. Further examples include butylated reaction product of p-cresol and dicyclopentadiene, substituted amine oligomers, N,N'-bis(2,2,6,6-tetramethyl-4-piperidinyl)-1,6-hexanediamine, 2,4-dichloro-6-(4-morpholinyl)-1,3,5-triazine, and N,N'-hexamethylene-bis[3-(3,5-di-t-butyl-4-hydroxyphenyl)propionamide]. Still further, transition metals or compounds thereof may function as ROD stabilizers, for instance iron, cobalt, nickel, ruthenium, rhodium, palladium, osmium, iridium, platinum, copper, manganese and zinc metal and compounds, as described in International Pub. No. WO 99/38914; U.S. Pat. No. 5,034,252; and U.S. Pat. No. 5,021,515.

The ROD stabilizer may also be an oxygen scavenging polymer, such as the polyketone polymers described in International Pub. No. WO 96/18686 of the formula

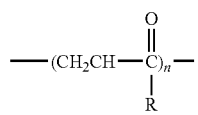

where R is H, an organic side chain or a silicon side chain, and n is a positive number greater than 2. Such polyketone ROD stabilizers are suitably employed in the thermoplastic composition in an amount of from 0.1% to about 10% by weight.

If their presence is desired, ROD stabilizers may be employed in the nanocomposites in any amount at least minimally effective in assisting in the resistance of the matrix material to degradation, i.e., in amounts of from about 0.01% to about 5%, suitably from about 0.1% to about 1%, for instance from 0.2% to 0.5%. The stabilizer can be compounded into the nanocomposite in the extrusion melt or in a separate compounding step prior thereto.

Many nanocomposites and nanoparticles are commercially available. Additionally, many methods of producing such nanocomposites and/or nanoparticles are known, and any of these maybe utilized to produce nanocomposites and nanoparticles for incorporation into the inventive device. Many such methods are disclosed and described, for example, in "Nanocomposites 2001, Delivering New Value to Plastics", Executive Conference Management, Jun. 25-27, 2001, Chicago, Ill., the entire disclosure of which is incorporated by reference herein for all purposes.

Advantageously, and since the filler particles can have an impact on the properties exhibited by the nanocomposite by virtue of the dispersion of the filler particles within the matrix, the particular method utilized to prepare the nanocomposite can be selected to assist in the provision of a medical device with the desired array of properties. That is, in certain medical device applications, it may be desirable to have the entirety of the medical device or medical device component exhibit the properties of the nanocomposite substantially uniformly throughout, or across the length of, the medical device. In such applications, it would be desirable to substantially uniformly distribute the filler particles throughout the matrix of the nanocomposite. In other applications, it may be desirable to have the entirety of the medical device or medical device component exhibit the properties of the nanocomposite, but at varying degrees throughout the device or component. In these applications, then, it would be desirable to vary the distribution of the filler particles throughout the matrix of the nanocomposite in a manner so that the desired varied properties are observed in the medical device or component.

For exemplary purposes only, then, processes for the production of such nanocomposites include polymerization of the matrix material in the presence of the filler, melt compounding of the matrix with the filler, and in-situ formation of the filler, e.g., as would be provided by the adding a silane monomer to a block copolymer and then curing the silane to produce nanostructured silica filler particles relatively uniformly dispersed within the in the matrix of the copolymer, to name a few. If a coupling/compatibilizing agent is to be used, it may be pre-coated onto the filler particles before compounding the filler particles with the matrix, or alternatively, the agents may be added during the nanocomposite formation process.

It has now been appreciated that these new nanomaterials can provide many unique advantages in the production of medical devices, i.e., certain desirable properties of nanomaterials can be exploited in ways particularly advantageous in the medical device industry.

First, the use of nanomaterials in the manufacture of medical devices can provide a greater amount of control to the manufacturer over at least some of the properties of the resulting medical device. In fact, the use of a nanomaterial in the inventive medical devices, either alone or in combination with one or more traditional materials, advantageously provides the opportunity to provide a variation in one or more properties within one or more dimensions of the inventive device than can be achieved in medical devices not comprising nanomaterials.

Further, a more subtle change in property and/or capability of a device can be seen by making a small change in the amount of nanoparticles within the device than can be seen when utilizing conventionally sized filler particles. This change in amount or density can be caused to occur within the inventive device. That is, if a nanomaterial is being utilized, for example, to provide strength to a length of medical device tubing or shafting, and it is desired that the strength of the tubing will decrease so that the tubing becomes more flexible at its proximal end, the load density of the nanoparticles within the length of tubing can be caused to change accordingly. Of course, such a load reduction can be caused to occur by reducing the amount of nanoparticles within the nanocomposite along the length of the tubing, or by simply altering the thickness of the tubing along its length.

Second, a lesser amount of filler material, relative to traditionally sized filler particles, can produce a similar property or provide a similar capability. The use of a lesser amount of material can translate to less material, shipping and storage cost, a savings that can be an important advantage in many medical device applications. Even in applications where a greater concentration of filler particles is desired, such highly filled nanocomposites are much easier to process than composites filled with the same concentration of conventionally sized particles.

Third, nanomaterials can, if desired, be comprised of materials traditionally used in the manufacture of medical devices, so long as the nanoparticles have a greatest dimension of less than about 1 micrometer when processed from such materials. The inclusion of these nanomaterials into a medical device comprising other non-nanomaterials is thus not likely to cause a lack of cohesiveness in the overall device due to incompatibility between the nanomaterial and non-nanomaterials. As a result, if desired, a variation in one or more properties of a multi-layered device could be provided by selecting and optimizing the number and organization of the layers, as well as the nanomaterials and non-nanomaterials to be used therein, to provide the properties or capabilities desired in the multilayer medical device.

Finally, the utilization of nanomaterials in the inventive medical devices advantageously can be used to provide optically clear medical devices that are yet radiopaque. That is, since in many cases the size of the nanoparticle is smaller than the wavelength of visible light, it is possible to use nanocomposite materials to manufacture a device that is transparent, and yet X-ray radiopaque. Other unique advantages that may be seen by the utilization of nanocomposites in the inventive medical devices include effects such as lowering the coefficient of friction, biocompatibility, and biodegradability, to name a few.

In light of the aforementioned newly identified and appreciated advantages, the present invention thus provides medical devices including at least one component comprising at least one nanomaterial. The present invention contemplates that the nanomaterial may be utilized as one or more of layers of a component, a component of a device in total, a device in total, or as a coating deposited over any portion of any of these.

The applicability of the inventive concept is not particularly limited to any particular class or grouping of medical devices. Rather, the identified advantages that can be seen are believed to be widely applicable, in whole or in part, to any medical device. It is believed, however, that the inventive concept will prove particularly advantageous when utilized in medical devices contemplated to be brought into therapeutic contact with a body, i.e., devices contemplated to be introduced into the body, either temporarily or permanently, for the purpose of effectuating a treatment or diagnosis thereof. Such devices find use in, e.g., urinary, cardiovascular, musculoskeletal, gastrointestinal, or pulmonary applications.

Medical devices useful in urinary applications include, for example, catheters, shunts, stents, etc. Exemplary medical devices useful in cardiovascular applications include stents, angiography catheters, coronary or peripheral angioplasty catheters (including over the wire, single operator exchange or fixed wire catheters), balloons, guide wires and guide catheters, real or artificial grafts, artificial vessels, artificial valves, filters, vascular closure systems, shunts, etc. Musculoskeletal medical devices include, for example, artificial ligaments, and prosthetics. One example of a medical device useful in a gastrointestinal application would be a shunt. Pulmonary medical devices include prosthetics, as one example.

Medical devices to which the inventive concept is believed to be particularly applicable include medical devices useful in any of the aforementioned applications, and that are introduced into the lumen of a patient. Such devices include, for example, catheters, embolic protection devices, grafts, shunts, stents, balloons, etc., for use in urinary, cardiovascular, musculoskeletal, gastrointestinal or pulmonary applications. Even more particularly, it is believed that the inventive concept will prove particularly advantageous when applied to medical devices intended to be introduced into a cardiovascular lumen for therapeutic purposes.

The present inventive medical device can, for example, be a catheter shaft, such as for an angiography system, angioplasty balloon, guide catheter, or stent delivery system. Such devices often include multiple lumens in a side-by-side or coaxial configuration. Coaxial configurations generally have inner and outer tubular components. According to the invention, the inner and/or outer tubular component of such a catheter can be formed from a nanomaterial. The inner and/or outer tubular components, in turn, can be comprised of a plurality of layers, in which case, one or more of the layers may comprise a nanomaterial. As mentioned hereinabove, and as is the case with any multi-layered medical device wherein at least one of the layers comprises a nanomaterial, the number and organization of the layers can be chosen and optimized to provide the properties or capabilities desired in the multilayer tubular component.

One particular example of a catheter shaft within the scope of the invention could comprise, for example, a nanocomposite further comprising carbon or ceramic nanofibers. Advantageously, such nanofibers could be utilized in applications wherein stainless steel braiding is currently utilized, thereby allowing for thinner walls than are possible with stainless steel braiding incorporated therein. Further, the utilization of ceramic or carbon nanofibers can result in a device that is detectable via MRI technology, whereas the presence of stainless steel braiding interferes with the image produced thereby. Finally, the increased surface area for contact between the nanofibers and the matrix material, as compared to the surface area for contact between a matrix material and stainless steel braiding, can result in a greater cohesion between the nanofibers and the matrix material.

Such shafting could be prepared by first spinning the nanofiber from the desired material, for example, by electrospinning or electrohydrodynamic spinning. Generally speaking, electrospinning uses electrical forces applied at the surface of a polymer solution or melt to create an electrically charged jet. When the jet dries or otherwise solidifies, electrically charged fiber remains. This technique can be used to produce patterns or braids from the electrically charged polymer jet by directing the charged jet onto a rod or tube, while rotating either or both of the spray nozzle, or the rod or tube onto which the material is deposited. Any strength enhancing polymer may be so processed and utilized in the inventive shafting, and polyacrylonitrile is but one example of a suitable polymer. Advantageously, and as is described in "Manufacturing, Characterization and Applications of Carbon Nanofibers", Yongkui Wen, Mat. Res. Soc. Symp. Proc, Vol.

702, the entire disclosure of which is hereby incorporated by reference for all purposes, the resulting polyacrylonitrile fibers can be carbonized to produce carbon fibers, which are from 20 to 100 times stronger than stainless steel fiber braiding. Once the nanofibers of the shafting have been so formed, a spray or dipcoat process can be used to provide the matrix material about the fiber network. Alternately, a nanocomposite comprising the nanofibers could be processed into the desired device utilizing normal extrusion, intermittent extrusion and/or by multi-layer extrusion.

Although described in connection with this particular exemplary embodiment of the present invention, the utilization of nanofibers, as well as the utilization of the electrospinning or spraying process to form them, or any other nanoparticles, followed by dipcoating, spraying, etc., to provide a matrix material, or component of the inventive device, about the fibers, is clearly within the scope of the present invention. For example, nanofibers, or a nanoparticle of any other geometry, form or shape, and comprising any material could be formed over a mold, and dipcoated or sprayed with, or welded to, a desirable matrix material, or component of an inventive device to produce any medical device to provide a medical device in accordance with the present invention.

A further example of a transluminal medical device that may benefit from application of the inventive concept would be a vessel graft. Such devices are known, and any of these, or vessel grafts developed in the future, may be improved by applying the inventive concept thereto. According to the invention, the graft may be artificial and may be prepared from, or coated with, a nanocomposite material, or may be real tissue. In either case, the graft may have a plurality of nanoparticles operatively disposed relative to a surface of the graft.

For example, and as described briefly hereinabove, a graft may be provided having disposed operatively relative thereto a magnetic wire. A plurality of nanoparticles comprising, for example, a magnetized biodegradable polymer and a therapeutic agent can be provided in conjunction with the graft. The graft can be implanted at a desired treatment site and the nanoparticles delivered systemically at any desired time to effectuate the delivery of the therapeutic agent to the treatment site. More particularly, the nanoparticles, once delivered via intraluminal fluid flow to an area in proximity to the graft, will be attracted and adhere to the graft via the magnetic materials present therein. The degradation of the biodegradable polymer will cause the site specific release of the therapeutic agent over time.

Yet another example of a transluminal medical device useful in cardiovascular applications that can be advantageously enhanced via application of the inventive concept is an embolic protection device, also know as a distal protection device, emboic filter, or simply as a filter. Many such devices are known, representative examples of which are described in commonly assigned U.S. Pat. Nos. 6,001,118 and 6,336,934, the disclosures of which are hereby incorporated by reference in their entirety and for all purposes.

Briefly then, and for purposes of illustration, embolic filters are utilized in transluminal cardiovascular applications wherein it is desired to collect floating debris, such as emboli. Generally, such filters have a collapsible body having a proximal inlet that allows blood, embolic material and/or other debris to enter the fiter and a distal outlet that allows the passage of blood therethrough, while yet retaining the embolic material and/or other debris within the filter body. Filters are desirably collapsible to a minimal profile for insertion into the luminal space from which emboli is desirably captured and removed, but yet, in order to be effective, desirably enlarge to approximate the inner diameter of the luminal space, i.e., so that substantially all emboli at least enters the filter body. Thus, filters are typically comprised of a thin material to provide the desired low profile, and yet, this thin material must be sufficiently robust to withstand collapsing, insertion and expansion within a luminal space. Further, once so expanded, filters are desirably comprised of a material having sufficient strength to withstand the pressure exerted by blood flowing and pulsing therethrough. Conventional filters, although acceptable, could yet be improved upon in these areas.

Application of the present inventive concept to embolic filters can provide such improvements. That is, by utilizing a nanomaterial in the production thereof, a thin filter can be produced that yet has sufficient elasticity, strength and robustness to perform satisfactorily under its demanding conditions of use. As but one example of this particular embodiment of the invention, an embolic filter can be produced utilizing a nanocomposite comprising a matrix material comprising polyurethane, such as Pellethane®, commercially available from the Dow Chemical Company, Midland, Mich., and nanoparticles comprising functionalized clay. More specifically, a filter can be prepared by dissolving the polyurethane in a suitable solvent, such as tetrahydrofuran, adding the clay nanoparticles thereto, and mixing the nanocomposite, e.g., in a high speed blender. The resulting nanocomposite can then advantageously be formed into an embolic filter by electrohydrodynamically spraying the nanocomposite onto a suitable mold or form. The resulting filler may advantageously comprise a substantially homogeneous dispersion of the clay nanoparticle due to the minimized droplet size distribution that can be seen utilizing electrohydrodynamic spraying as opposed to conventional electrostatic spraying. Further, the resulting filter can be three times thinner and yet many times stronger than an embolic filter prepared from conventional materials.

Referring now to FIGS. 1 and 2, there is illustrated such an embolic filter embodying principles of the present invention. More particularly, FIGS. 1 and 2 illustrate embolic protection device 10 for collecting loosened debris in a body lumen, FIG. 1 illustrating device 10 in a closed collapsed profile, for insertion into a bodily lumen, while FIG. 2 illustrates device 10 in an open, radially expanded profile for collecting debris from a bodily lumen.

Device 10 includes a filter membrane 102 and a collapsible proximally tapered frame 104. Frame 104 supports filter membrane 102 and is operably coupled to an elongated guidewire 106 or other support device. Frame 104 includes an orifice 108 and a plurality of longitudinally extending support ribs 110. In the expanded profile illustrated in FIG. 2, orifice 108 is opened and support ribs 110 extend radially outwardly to support orifice 108. Collar 112 movably couples the proximal ends of ribs 110 to guidewire 114. Orifice 108 is thus coupled to collar 112 through ribs 110 and is movable between the collapsed profile illustrated in FIG. 1 and the opened deployed profile illustrated in FIG. 2.

Filter membrane 102 is generally cone-shaped, having a proximal end 114 and distal end 116. Distal end 116 is preferably tapered so as to meet the diameter of guidewire 106 and is preferably fixedly secured or formed to guidewire 106. Proximal end 114 has a larger diameter than distal end 116, preferably approximately equivalent to the diameter of orifice 108, and is coupled thereto. According to the present invention, filter membrane 102 is formed from a nanocomposite material, such as the polyurethane/clay nanocomposite material discussed hereinabove, and has a plurality of small openings 118 provided therein. Openings 118 may be formed in the nanocomposite membrane by known laser techniques and are desirably sized in order to allow blood to flow therethrough, while restricting the flow of debris or emboli, preferably retaining such debris or emboli within filter membrane 102.

Orifice 108 is generally formed of a pleated ring 120 having an expanded dimension to support filter membrane 102 in the opened deployed profile as illustrated in FIG. 1 and a collapse dimension to support the filter in the closed collapsed profile as illustrated in FIG. 2. Pleated ring 120 is collapsed by closing folds 122 as illustrated by arrows 124 so that adjacent folds 122 are positioned in close proximity. In such a position, orifice 108 assumes a relatively small dimension to collapse filter membrane 102 for insertion into, and retrieval from, an intraluminal space.

Referring now to FIGS. 3 and 4, there is illustrated an embodiment of a medical device embodying principles of the present invention. In particular, FIG. 3 is a longitudinal cross-section view of the distal end of a balloon angioplasty catheter 30. In this embodiment, catheter 30 includes an inner tubular component 330 comprising an inner layer 332 and outer layer 334. A balloon 336 having a distal waist 338 is attached to inner tubular component 330. Balloon 336 also has a proximal waist 340 attached to outer tubular component 342. A guidewire 344 is shown within lumen 346 of inner tubular component 330. FIG. 4 is a transverse cross-section view taken at line 4-4 of FIG. 3.

According to the invention, it will be appreciated that inner tubular component 330, including either or both of inner layer 332 and outer layer 334, outer tubular component 342, balloon 336, or guidewire 344, may be prepared from, or may comprise, a nanomaterial as disclosed herein. Furthermore, balloon 336 may have a stent (not shown) disposed operatively relative thereto, in order to provide that catheter 30 may also function as a stent delivery system. In such an embodiment, the stent, as well as any other components that may desirably be included in such a stent delivery device, may comprise a nanomaterial.

In addition to the inventive devices themselves, the present invention also provides methods of making the inventive devices. Generally speaking, the method involves providing a nanomaterial and processing the nanomaterial to form at least a portion of at least a component of a medical device. The nanomaterial may be obtained from any of a variety of commercial sources of such materials, or, it may be prepared from the desired components thereof by any method. The device or component thereof may then be manufactured or processed using the nanomaterial according to any suitable method, including at least those methods utilized to manufacture the corresponding non-filled medical device, or a corresponding medical device comprising a composite material further comprising traditionally sized filler particles. There are a multiplicity of methods for the manufacture of medical devices that are thus appropriate, examples of which include, but are not limited to, foam processing, blow molding or film molding, sheet forming processes, profile extrusion, rotational molding, compression molding, thermoset pre-preg processes, electrospinning or spraying, electrohydrodynamic spinning or spraying, and reaction injection molding processes.

Furthermore, medical devices in accordance with the present invention can be provided with enhanced properties or capabilities due to the inclusion of at least one nanomaterial therein, which properties and capabilities, in turn, are expected to render the inventive medical devices particularly advantageous to use in therapeutic treatments. As a result, the present invention also provides methods of medical care utilizing the inventive devices. Generally speaking, the inventive method comprises providing a medical device comprising at least one nanomaterial, and utilizing the device to perform a diagnostic or therapeutic treatment. In those embodiments of the invention wherein the device is a device intended to be introduced into a cardiovascular lumen, the method may further comprise inserting the device into the lumen and advancing it to the desired treatment site. As desired, the method may further comprise the delivery of the device to the treatment site, as may be the case with a stent, or performance of a desired treatment and removal of the device from the lumen, as may be the case with an angioplasty catheter.

Advantageously, in embodiments where the systemic, controlled delivery of therapeutic agents is desired, the method may comprise the steps of delivering a device followed either relatively immediately, or after a delay, by the systemic delivery of nanoparticles comprising a material capable of adhering to the delivered device, the therapeutic agent desirably delivered, and a means for causing the delivery of the therapeutic agent from the nanoparticles to the treatment site, e.g., a biodegradable material.

The invention will now be further illustrated in the following examples, which are not intended to be limiting, but rather, have been chosen and described so that others skilled in the art may appreciate and understand the principles and practices of the present invention.

EXAMPLE 1

Preparation of Inner Shaft Catheter Tubing with an HDPE/POSS Nanocomposite

1) Preparation of the HDPE/POSS Nanocomposite by Twin-Screw Extrusion Compounding.

An organically functionalized POSS (MS0830, an OctaMethyl-POSS commercially available from Hybrid Plastics, Fountain Valley, Calif.) was compounded with high density polyethylene (HDPE Marlex 4903, commercially available from Chevron-Phillips Chemical Company, Houston, Tex.), In particular, a material feed ratio of HDPE to POSS of 4:1 was fed into a counter rotating dispersive twin screw compounder ZSE 27 (commercially available from Leistritz Company, Allendale, N.J.) operating at 190° C. and a speed of 200 RPM. The compounding output was at 5 pounds per hour.

2) Extrusion of Inner Shaft Catheter Tubing Incorporating HDPE/POSS Nanocomposite Material.

A 4:1 mixture of the HDPE/POSS nanocomposite to Plexar® 390 anhydride modified polyethylene (commercially available from Equistar Chemical Company, Houston, Tex.) was premixed and further diluted at a 3:1 ratio with Marlex 4903 polyethylene and extruded into tubing of dimensions of 0.018 inch×0.024 inch at 220° C.

EXAMPLE 2

Preparation of Outer Shaft Catheter Tubing with a Pebax®/POSS Nanocomposite

1) Preparation of the Pebax®/POSS Nanocomposite by Twin-Screw Extrusion Compounding.

An organically functionalized POSS (AM0265, an Aminopropylisobutyl-POSS commercially available from Hybrid Plastics) was compounded with Pebax® 7233 (Pebax® is a polyether block amide commercially available from Atofina, Brussels, Belgium). In particular, a material feed ratio of Pebax® to POSS of 4:1 was fed into a counter rotating dispersive Leistritz ZSE 27 twin screw compounder operating at 200° C. and a speed of 100 RPM. The compounding output was at 5 pounds per hour.

2) Extrusion of Outer Shaft Catheter Tubing Incorporating Pebax®/POSS Nanocomposite Material.

A 3:1 dilution of the Pebax®/POSS nanocomposite to Pebax® 7233 was prepared and extruded into outer shaft tubing with dimensions of 0.0306 inch×0.0362 inch at 226° C.

It is expected that, during the tubing extrusion process, the nanocomposite will be more stable than conventional filled Pebax®. It is further believed that, if the tubing produced by this method were subject to an EtO sterilization, that the POSS nanofiller will reduce or substantially prevent the oriented Pebax®& chains from relaxing to a detrimental degree, as compared to such relaxation that would be expected to occur in an unfilled Pebax® medical device or device component when subjected to such sterilizing treatment.

EXAMPLE 3

Preparation of Outer Shaft Catheter Tubing with a Pebaxt®/Clay Nanocomposite

A Pebax®/clay nanocomposite material said to contain 95% Pebax® 7233 and 5% clay filler with the trade designation of 2099×83109 C was purchased from RTP Company (Winona, Minn.). The material was extruded into acceptable outer shaft tubing with dimensions of 0.0306 inch×0.0362 inch at an extrusion temperature of 226° C.

EXAMPLE 4

Preparation of Multilayer Tubing with a Pebax®/Montmorillonite Nanocomposite

A Pebax®/montmorillonite nanocomposite material containing 95% of a 72 durometer Pebax® material (such as Pebax® 7233 commercially available from Atochem) and 5% montmorillonite filler will be compounded with a twin screw extruder as described above. The nanocomposite material will then be coextruded with non-filled Pebax® at a temperature sufficient to provide appropriate viscosity for extrusion, i.e., from about 190° C. to about 215° C., into acceptable trilayer tubing having the Pebax®/montimorillonite nanocomposite as a middle layer and non-filled Pebax® as the inner and outer layers. The trilayer tubing will have dimensions appropriate for the intended use of the tubing. If the tubing is to be used, e.g., in the formation of a balloon, suitable dimensions would be an inner diameter of about 0.0176 inch and an outer diameter of about 0.342 inch.

EXAMPLE 5

Preparation of Monolayer Tubing with a Pebax®/Modified Montmorillonite Nanocomposite A Pebax®/montmorillonite nanocomposite material containing 90% of a 70 durometer Pebax® material (such as Pebax® 7033 commercially available from Atochem) and 10% modified montmorillonite filler will be compounded with a twin screw extruder as described above. Prior to compounding, the montmorillonite will be modified with a functionalizer comprising a block copolymer capable of interacting with polyether and/or polyamide, as described hereinabove. The nanocomposite material will be extruded at a temperature sufficient to provide appropriate viscosity for extrusion, i.e., from about 190° C. to about 215° C., into acceptable monolayer tubing having dimensions appropriate for the intended use of the tubing. This tubing can then be used to form balloons, the inner lumen of catheters, the outer lumen of catheters, and the like. If the tubing is to be used, e.g., in the formation of a balloon, suitable dimensions would be an inner diameter of about 0.0176 inch and an outer diameter of about 0.342 inch.

EXAMPLE 6

Preparation of Monolayer Tubing with a Nylon 12/Modified Montmorillonite Nanocomposite A nylon 12/montmorillonite nanocomposite material containing 99% of a nylon 12 (commercially available under the tradename Rilsan® from Atofina) and 1% Modified montmorillonite filler will be prepared as follows. All materials will either be purchased as powders or ground into powders by any known method. The montmorillonite will be modified with a functionalizer comprising block polyamide or any material having polyamide groups, as described hereinabove. The powdered nylon 12 and powdered functionalized montmorillonite will be mixed together and fed into an extrusion process via a gravimetric feeding device (or any other acceptable powder feeding mechanism). The nanocomposite material will then be extruded at a temperature sufficient to provide appropriate viscosity for extrusion, i.e., from about 210° C. to about 240° C., typically 220° C. to 230° C., into acceptable monolayer tubing having dimensions appropriate for the intended use of the tubing. Such uses could include, e.g., formation of balloons, inner lumens of catheters, outer lumens of catheters, etc. Tubing comprising such a nanocomposite is contemplated to be particularly useful in the formation of balloons, for which use appropriate tubing dimensions are an inner diameter of about 0.0176 inch and an outer diameter of about 0.342 inch.

EXAMPLE 7

Preparation of Monolayer Tubing with a Polyurethane/Carbon Nanofiber Nanocomposite Polyacrylonitrile will be electrospun about a rod or tube of the desired tubing dimensions.

The resulting polyacrylonitrile fibers will be heated in air, causing it to oxidize. The resulting modified polyacrylonitrile fibers will then be heated in the absence of air to a temperature greater than at least about 1300° C. This process will cause the carbonization of the fibers into the form of ribbon like fused ring polymer, which will then condense to provide a lamellar basal plane structure of nearly pure carbon.

A polyurethane will be dissolved in an amount of tetrahydrofuran. The carbon nanofiber structure will be dipcoated with the polyurethane/tetrahydrofuran solution multiple times so as to create a polyurethane matrix surrounding the carbon nanofiber structure, thereby forming acceptable monolayer tubing having dimensions appropriate for the intended use of the tubing.

This tubing can then be used to form balloons, the inner lumen of catheters, the outer lumen of catheters, and the like. If the tubing is to be used, e.g., in the formation of a balloon, suitable dimensions would be an inner diameter of about 0.0176 inch and an outer diameter of about 0.342 inch.

EXAMPLE 8

Preparation of an Embolic Filter with a Pellethane®/Functionalized Clay Nanocomposite A suitable Pellethane® will be dissolved in a corresponding suitable amount of tetrahydrofuran. An amount of alkylammonium-modified montmorillonite, up to 40%, will be added to the Pellethane® solution, and the solution mixed in a high speed mixer operatively disposed relative to an ultrasonic transducer until microscopic inspection reveals that the clay is dispersed and that no clots thereof remain.

The Pellethane®/montmorillonite nanocomposite will then be electrostatically sprayed onto a suitable mold until the desired thickness is achieved. In particular, it is believed that an embolic filter so produced and having a thickness of about 0.0003", about 4 times less thick than a filter comprising a traditional material, will yet exhibit up to a 300% increase in mechanical strength over filters prepared from conventional materials.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims.

What is claimed is:

1. An intravascular balloon catheter comprising:
   an outer tubular member having a proximal end and a distal end;
   an inner tubular member disposed coaxially within the outer tubular member, the inner tubular member having a proximal end and a distal end and including an inner layer, an outer layer, and an intermediate layer disposed therebetween; and
   an inflatable balloon having a proximal waist and a distal waist, wherein the balloon is attached proximate the distal end of the outer tubular member at the proximal waist and the balloon is attached proximate the distal end of the inner tubular member at the distal waist;
   wherein at least one of the inner or outer layers of the inner tubular member includes a nanocomposite material comprising a matrix material and a first plurality of nanoparticles comprising carbon nanotubes or carbon nanofibers; and
   wherein the intermediate layer comprises a second plurality of nanoparticles.

2. The balloon catheter of claim 1, wherein the matrix material comprises a thermoplastic or a thermoset polymer.

3. The balloon catheter of claim 1, wherein the first plurality of nanoparticles further comprise a clay.

4. The balloon catheter of claim 3, wherein the clay comprises montmorillonite.

5. The balloon catheter of claim 1, wherein the first plurality of nanoparticles further comprise either octamethyl polyhedral oligomeric silsesquioxane or aminopropylisobutyl polyhedral oligomeric silsesquioxane.

6. The balloon catheter of claim 1, wherein the nanocomposite further comprises a functionalizer.

7. The balloon catheter of claim 6, wherein the functionalizer is alkylammonium.

8. An intravascular balloon catheter comprising:
   an outer tubular member having a proximal end and a distal end;
   an inner tubular member having an inner layer, an outer layer, and a tie layer disposed therebetween, the inner tubular member disposed coaxially within the outer tubular member, and the inner tubular member having a proximal end and a distal end; and
   an inflatable balloon having a proximal waist and a distal waist, wherein the balloon is attached proximate the distal end of the outer tubular member at the proximal waist and the balloon is attached proximate the distal end of the inner tubular member at the distal waist;
   wherein the inner layer and the outer layer of the inner tubular member each comprise a nanocomposite material; and
   wherein the tie layer comprises nanoparticles, the nanoparticles comprising carbon nanotubes, ceramic nanotubes, carbon nanofibers, or ceramic nanofibers.

9. The balloon catheter of claim 8, wherein the nanocomposite material comprises a thermoplastic or thermoset matrix material and at least one plurality of nanoparticles.

10. The balloon catheter of claim 9, wherein the nanoparticles comprise a clay.

11. The balloon catheter of claim 9, wherein the nanocomposite material comprises at least two pluralities of nanoparticles.

12. The balloon catheter of claim 9, wherein the nanocomposite material further comprises a functionalizer.

13. The balloon catheter of claim 8, wherein the inner layer and the outer layer each comprise a different nanocomposite.

14. An intravascular balloon catheter comprising:
   an outer tubular member having a proximal end and a distal end;
   an inner tubular member having an inner layer, an outer layer, and a tie layer disposed therebetween, the inner tubular member disposed coaxially within the outer tubular member, and the inner tubular member having a proximal end and a distal end; and
   an inflatable balloon having a proximal waist and a distal waist, wherein the balloon is attached proximate the distal end of the outer tubular member at the proximal waist and the balloon is attached proximate the distal end of the inner tubular member at the distal waist;
   wherein the inner tubular member includes a nanocomposite material, the nanocomposite material having a polymeric matrix material, at least one plurality of clay nanoparticles, and a functionalizer; and
   wherein the tie layer comprises carbon nanotubes, ceramic nanotubes, carbon nanofibers or ceramic nanofibers.

* * * * *

UNITED STATES PATENT AND TRADEMARK OFFICE
CERTIFICATE OF CORRECTION

PATENT NO. : 8,137,373 B2
APPLICATION NO. : 12/418849
DATED : March 20, 2012
INVENTOR(S) : Jan Weber Page 1 of 1

It is certified that error appears in the above-identified patent and that said Letters Patent is hereby corrected as shown below:

Column 1
Line 46: delete "Ofiten" and insert therefor -- Often --.

Column 6
Line 15: delete "1000 mm" and insert therefor --1000 nm --.
Line 15: delete "750 mm" and insert therefor -- 750 nm --.
Line 16: delete "1 mm" and insert therefor -- 1 nm --.
Line 17: delete "100 mm" and insert therefor -- 100 nm --.

Column 11
Line 33: delete "P-(3,5-di-*t*-butyl-6-hydroxyphenyl)" and insert therefor
-- β-(3,5-di-*t*-butyl-6-hydroxyphenyl) --.

Column 15
Line 52: delete "emboic" and insert therefor -- embolic --.
Line 62: delete "fiter" and insert therefor -- filter --.

Column 19
Line 23: delete "Pebaxt®" and insert therefor -- Pebax® --.

Signed and Sealed this
Twenty-sixth Day of June, 2012

David J. Kappos
*Director of the United States Patent and Trademark Office*